United States Patent

Tsukamoto et al.

[11] 4,192,880
[45] Mar. 11, 1980

[54] 2-SUBSTITUTED BENZIMIDAZOLE COMPOUNDS

[75] Inventors: Goro Tsukamoto, Toyonaka; Koichiro Yoshino, Settsu; Toshihiko Kohno, Sakai; Masahiro Taguchi, Settsu; Katsumi Dezawa, Settsu; Hajime Kagaya, Settsu; Keizo Ito, Osaka; Takashi Nose, Suita, all of Japan

[73] Assignee: Kanebo, Ltd., Tokyo, Japan

[21] Appl. No.: 949,429

[22] Filed: Oct. 10, 1978

Related U.S. Application Data

[62] Division of Ser. No. 856,969, Dec. 2, 1977.

[30] Foreign Application Priority Data

Apr. 7, 1977 [JP] Japan ............................ 52-40072

[51] Int. Cl.² ................ A61K 31/415; C07D 235/08
[52] U.S. Cl. ............................ 424/273 R; 548/334; 546/271; 424/263
[58] Field of Search .................... 260/296 B; 548/334; 424/273 R

[56] References Cited

FOREIGN PATENT DOCUMENTS 1555336 12/1968 France ................................ 260/296 B
1021393 3/1966 United Kingdom ..................... 548/334

OTHER PUBLICATIONS

Otaki et al., Yakugasku Zasshi, vol. 85, pp. 926 to 935 (1965).
Ridley et al., J. Heterocyclic Chem., vol. 2, pp. 453 to 456 (1965).
Osone et al., Chem. Abst., vol. 65, cols. 10577-10578 (1966).
Bachetti et al., Chem. Abst., vol. 52, cols. 15511-15512 (1958).
Farb. Bayer Akt.-Ges., Chem. Abst., vol. 53, col. 2256 (1959).
C. H. Boehringer Sohn, Chem. Abst., vol. 53, col. 4317 (1959).
Rao et al., Chem. Abst., vol. 51, cols. 8730-8731 (1957).
Ciba, Ltd., Chem. Abst., vol. 58, Abst. of Brit. Pat. No. 901,648, col. 2455 (1963).
Brown et al., Chem. Abst., vol. 58, col. 2456 (Abst. of U.S. Pat. No. 3,055,907) (1963).
Fara et al., Chem. Abst., vol. 65, col. 10984 (1966).
Ridi et al., Chem. Abst., vol. 70, Abst. 87668 (1969).
ICI, Chem. Abst., vol. 60, col. 15687 (Abst. of Belg. Pat. No. 631,490).
Shiggo, Chem. Abst., vol. 69, No. 36089z (1968).
Balyaev et al., Chem. Abst., vol. 74, Abst. No. 53650w (1971).
Reddy et al., Chem. Abst., vol. 72, Abst. No. 31695w (1970).
Hofmann, Imidazole and Its Derivatives, Part I, pp. 260 to 267, Interscience Publishers, Inc. NY (1953).
Simonov et al., Chem. Abst., vol. 68, Abst. No. 105088s (1968).

Primary Examiner—John D. Randolph
Attorney, Agent, or Firm—Haight & Huard

[57] ABSTRACT

2-Substituted benzimidazole compounds of the formula:

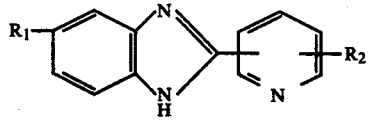

(I)

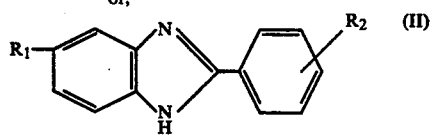

(II)

wherein $R_1$ is hydrogen, halogen, lower alkyl or lower alkoxy, and $R_2$ is hydrogen or lower alkyl with the proviso that $R_1$ and $R_2$ do not stand for hydrogen simultaneously and, when $R_1$ is hydrogen, $R_2$ cannot mean a methyl group at 6th position on the pyridin-2-yl group or methyl an isobutyl group on the phenyl group; are useful as anti-inflammatory agents and/or analgesics.

12 Claims, No Drawings

2-SUBSTITUTED BENZIMIDAZOLE COMPOUNDS

This is a division of application Ser. No. 856,969, filed Dec. 2, 1977.

This invention relates to certain 2-substituted benzimidazole compounds, and to process for their preparation.

The compounds of this invention can be represented by the following general formula:

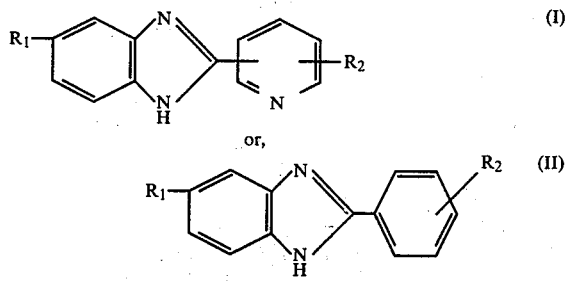

wherein $R_1$ is hydrogen, halogen, lower alkyl or lower alkoxy, and $R_2$ is hydrogen or lower alkyl with the proviso that $R_1$ and $R_2$ do not stand for hydrogen simultaneously and, when $R_1$ is hydrogen, $R_2$ cannot mean a methyl group at 6th position on the pyridin-2-yl group or an isobutyl group on the phenyl group.

The terms "lower alkyl" and "lower alkoxy" used herein mean those of $C_1$ to $C_4$.

The compounds of this invention are pharmceutically active agents. They are useful as anti-inflammatory agents and/or analgesics.

These compounds of Formula I can be conveniently prepared by reacting a compound of the formula

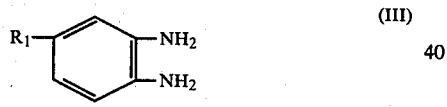

in which $R_1$ is as defined thereto in Formulae I, or an acid-addition salt thereof with a compound of the formula:

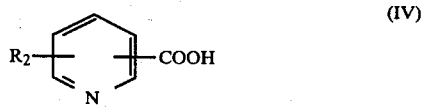

wherein $R_2$ is as defined thereto in Formula I, in the presence of a condensation agent preferably under a current of nitrogen gas. Examples of preferred condensation agents include polyphosphoric acid, polyphosphoric esters, hydrochloric acid, hydrobromic acid and boric acid. The reaction may be carried out, if desired, in an inert solvents such as O-dichlorobenzene, nitrobenzene or diglyme. Polyphosphoric acid and its esters are most preferable for this reaction because they give the compounds I in a higher yield by simply diluting the reaction mixture with water and neutralizing.

The starting O-phenylene diaminers III, particularly those having an electron releasing group are unstable and would encounter difficulties in handling thereof. These difficulties may be overcome by using their stable acid-addition salts in the reaction for the synthesis of the benzimidazole compounds I having an electron releasing group on the benzene ring.

Alternatively the compounds of Formula I may be prepared by reacting the starting compound III with a cyanopyridine of the formula:

wherein $R_2$ is as defined in Formula I, in a polar solvent firstly under basic conditions and then under weakly acidic conditions. Examples of preferred polar solvents include dimethylformamide, dimethylacetamide, N-methylpyrrolidone, hexamethylphosphoramide, dimethylsulfoxide, methanol, ethanol and the like. Examples of bases which may be used in the above reaction include alkali metal alkoxide such as sodium methoxide, sodium ethoxide or potassium t-butoxide.

Examples of weak acids which may be used in the above reaction include acetic acid, citric acid, oxalic acid or carbonic acid. The reaction may be preferably carried out by heating the reactants III and V in a polar solvent in the presence of a base at the boiling temperature of the solvent for 15 minutes to several hours, adding a weak acid to the reaction mixture to make the mixture weakly acidic and continuing the reaction at a temperature from 60° C. to the boiling point of the solvent.

The benzimidazole compounds of the formula:

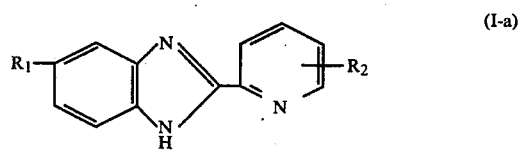

wherein $R_1$ and $R_2$ are as defined in Formula I, may be advantageously prepared by reacting the starting compound III with α-picoline or its alkylated derivative of the formula:

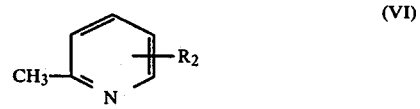

wherein $R_2$ is as defined, in the presence of sulfur. This reaction is advantageous in that easily available α-picoline or its derivatives may be used as such. The reaction may be performed either without using any solvent or in an inert solvent such as O-dichlorobenzene or diglyme. Usally 1 to 1.5 moles of the compound VI and 1.5 to 3 moles of sulfur are used for one mole of the starting compound III.

The compounds of Formula II can be prepared by reacting the compound of Formula III or its acid-addition salt with a compound of the formula:

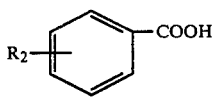

(VII)

wherein $R_2$ is as defined, in the presence of a condensation agent preferably under a current of nitrogen gas. Examples of preferred condensation agents include polyphosphic acid, its esters, hydrochloric acid, hydrobromic acid and boric acid. The reaction may be carried out, if desired, in an inert solvent such as O-dichlorobenzene, nitrobenzene or diglyme. Polyphosphoric acid and its esters are most preferable because they give the compound II in a higher yield by simply diluting the reaction mixture with water and neutralizing.

The compounds of Formula II may also be prepared by reacting the starting compound III with a compound of the formula:

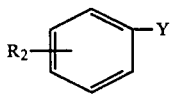

(VIII)

wherein $R_2$ is as defined, and Y is —CN, —CSSH, —CHO or COOR wherein R is $C_1$–$C_4$ alkyl, in a polar solvent firstly under basic conditions and then weakly acidic conditions. Examples of preferred polar solvents include dimethylformamide, dimethylacetamide, N-methylpyrrolidone, hexamethylphosphoramide, dimethylsulfoxide, methanol, ethanol and the like. Examples of bases which may be used in the above reaction include alkali metal alkoxide such as sodium methoxide, sodium ethoxide, or potassium t-butoxide. Examples of acids which may be used in the above reaction include acetic acid, citric acid, oxalic acid, carbonic acid, hydrochloric acid or hydrobromic acid, and acetic acid is most preferable. The reaction may be preferably carried out by heating the reactants III and VIII in a polar solvent in the presence of a base at a temperature from room temperature to the boiling point of the solvent, adding an acid to the reaction mixture to make the mixture weakly acidic and continuing the reaction at a temperature from 60° C. to the boiling point of the solvent.

Alternatively the compounds of Formula II may be prepared via a compound of the formula:

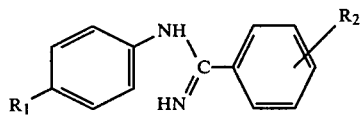

(IX)

wherein $R_1$ and $R_2$ are as defined thereto in Formula II.

The intermediate compounds IX may be conveniently prepared by reacting a compound of the formula:

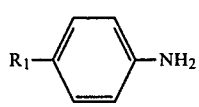

(X)

wherein $R_1$ is as defined, with a compound of the formula:

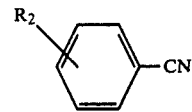

(XI)

wherein $R_2$ is as defined, in the presence of aluminum chloride as a catalyst in an inert solvent such as mono - or dichlorobenzene or tetrachloroethane at an elevated temperature from 100° to 200° C.

Another route for the synthesis of the compounds IX comprises the steps of reacting the compound XI with anhydrous methanol or ethanol under acidic conditions to give a compound of the formula:

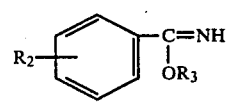

(XII)

wherein $R_2$ is as defined and $R_3$ is methyl or ethyl, and reacting the resulting compound XII with the compound X in a solvent to give the compound IX. This route is advantageous when the aniline compound X has an electron releasing group and hence is reactive.

The resulting amidine compounds IX may be then cyclized by reacting with a halogenating agent in an aqueous medium under acidic conditions and then treating the resulting compound with an alkali under heating. Examples of preferred aqueous medium include mixtures of water with a water-miscible organic solvent such as methanol, ethanol, dimethylsulfoxide or dioxan. Examples of preferred halogenating agent include hypochlorites, t-butylhypochlorite and the like. The halogenation reaction is conveniently carried out in the presence of an acid such as hydrochloric acid under cooling with ice or at room temperature. The resulting N-haloamidine compounds may be isolated from the reaction mixture by the extraction with a solvent thereof such as methylene chloride and subjected to the cylizing reaction. The reaction mixture containing the N-haloamidines may be used as such.

Examples of preferred alkali include sodium carbonate, potassium carbonate, sodium hydroxide and potassium hydroxide.

The compounds of this invention have useful pharmacological effects. To illustrate the anti-inflammatory activity of these compounds, the compounds indicated in the following table were administered orally at a dose of 100 mg/kg to male Wistar rats weighing 110 to 130 g. Edema was induced on the foot of animals inaccordance with the method described in "Proceedings of the Society for Experimental Biology and Medicine" 111, 544 (1962).

Percents of inhibition of edema after 3 hours were determined.

The data obtained are shown in the following table.

Table I

| Compound | % Inhibition |
| --- | --- |
| 2-(5-ethylpyridin-2-yl)benzimidazole | 50 |
| 2-(6-ethylpyridin-2-yl)benzimidazole | 42 |
| 2-(6-methylpyridin-2-yl)-5(6)-methylbenzimidazole | 48 |
| 2-(6-methylpyridin-2-yl)-5(6)-methoxybenzimidazole | 60 |
| 2-(6-methylpyridin-2-yl)-5(6)-chlorobenzimidazole | 65 |
| 2-(p-ter-butylphenyl)benzimidazole | 44 |
| 2-(p-ethylphenyl)benzimidazole | 58 |

Table I-continued

| Compound | % Inhibition |
| --- | --- |
| 2-(p-ethylphenyl)-5(6)-methoxybenzimidazole | 88 |
| 2-(o-ethylphenyl)-5(6)-methoxybenzimidazole | 70 |
| 2-(m-ethylphenyl)benzimidazole | 56 |
| phenylbutazone | 43 |

As indicated in the foregoing table, the compounds of this invention significantly exceeded the well known anti-inflammatory agent phenylbutazone.

The compounds of the invention may be used in warm-blooded animals, particularly mammals, as medicaments in the form of pharmaceutical compositions containing the compounds in admixture or conjunction with a pharmaceutical organic or inorganic, solid or liquid carrier for oral, rectal, or parenteral administration.

The total daily doses can vary from about 1 mg./kg. to about 10 mg./kg.

The preferred route of administration is the oral route. Suitable compositions include, without limitation, tablets, capsules, powders, solutions, suspensions, sustained release formulations and the like.

To produce dosage units for peroral application, the compositions of this invention may be combined, e.g., with solid pharmaceutically acceptable pulverulent carriers such as lactose, saccharose, sorbitol, mannitol; starches such as potato starch, corn starch or amylopectin, also laminaria powder or citrus pulp powder, cellulose derivatives or gelatin, also lubricants such as magnesium or calcium stearate or polyethylene glycols of suitable molecular weights may be added, to form tablets or press coated tablets. The latter are coated for example, with concentrated sugar solutions which can contain e.g., gumarabic talcum and/or titanium dioxide, or they are coated with lacquer dissolved in easily volatile organic solvents or a mixture of organic solvents.

Dyestuffs can be added to these coatings, for example, to distinguish between different contents of active substances.

Hard gelatin capsules contain, for example, granulates of the instant composition with solid pulverulent carriers such as, e.g., lactose, saccharose, sorbitol, mannitol and further starches such as potato starch, corn starch or amylopectin, cellulose derivatives or gelatin, as well as magnesium stearate or stearic acid.

Suppositories containing a compound of the present invention are readily obtained by techniques well known to those skilled in the art of compounding dosage forms. A compound of the present invention is dispersed in a carrier such as cocoa butter and the suppositories formed in the usual way.

The compounds of this invention and their preparation are more fully illustrated by the following examples. These examples are included here for the purpose of illustration and are not intended as a limitation.

EXAMPLE 1

Preparation of 2-(5-methylpyridin-2-yl)benzimidazole 6.2 g. of o-phenylenediamine, 7.1 g. of 5-methylpicolinic acid and 40 g. of polyphosphoric acid were stirred under nitrogen gas current at 160° C. to 180° C. for 4 hours. To the reaction mixture were added 400 ml. of water and then a concentrated aqueous solution of sodium carbonate to neutrality. The resulting crystals were filtered off, dried and recrystallized from acetonitrile or ethyl acetate to obtain 9.4 g. of colorless needles of the product (86% of theory), M.P. 229.0°–229.5° C.

EXAMPLE 2

Preparation of 2-(2-methylpyridin-5-yl) benzimidazole 11.9 g. of o-phenylenediamine, 13.7 g. of 2-methylpyridine-5-carboxylic acid and 100 g. of polyphosphoric acid were stirred under nitrogen gas current at 180° C. to 200° C. for 4 hours. To the reaction mixture were added 800 ml. of water and then a concentrated aqueous solution of sodium carbonate to neutrality. The resulting crystals were filtered off, dried and recrystallized from acetonitrile to give 15.7 g. of colorless needles of the product (75% of theory), M.P. 265.5°–266.0° C.

EXAMPLE 3

Preparation of 2-(3-methylpyridin-2-yl)benzimidazole 15.0 g. of o-phenylenediamine, 15.0 g. of 2,3-lutidine and 13.5 g. of sulfur powder were heated at 160°–170° C. for 8 hours.

To the reaction mixture was added 200 ml. of methanol. The mixture was filtered to remove sulfur powder and evaporated in vacuo to remove the solvent. The residue was subjected to silica gel column chromatography and recrystallized from cyclohexane.

22.6 g. of colorless needles of the product (77% of theory) was obtained. M.P. 159.5°–160° C.

EXAMPLE 4

Preparation of 2-(2-methylpyridin-4-yl) benzimidazole 3.4 g. of o-phenylenediamine, 4.4 g. of 2-methylisonicotinic acid and 30 g. of polyphosphoric acid were heated at 190°–200° C. under nitrogen gas current for 4 hours with stirring.

The reaction mixture was diluted with 500 ml. of water and then neutralized with sodium carbonate. The resulting crystals were filtered off, dried and recrystallized from ethyl acetate to give 5.5 g. of colorless needles of the product (82% of theory). M.P. 205°–206° C.

EXAMPLE 5

Preparation of 2-(5-ethylpyridin-2-yl) benzimidazol 11.3 g. of o-phenylenediamine, 15.1 g. of 5-ethylpicolinic acid and 80 g. of polyphosphoric acid were heated at 180°–190° C. under nitrogen gas current for 3 hours with stirring. The reaction mixture was diluted with 1,000 ml. of water and then neutralized with sodium carbonate. The resulting crystals were filtered off, dried and recrystallized from ethyl acetate to give 17.1 g. of colorless needles of the product (78% of theory). M.P. 172.5°–173.° C.

Analysis calculated for $C_{14}H_{13}N_3$: C, 75.31; H, 5.87; N, 18.82. Found: C, 75.51; H, 5.75; N, 18.68.

EXAMPLE 6

Preparation of 2-(5-ethylpyridin-2-yl)benzimidazole 130 g. of o-phenylenediamine, 121 g. of 5-ethyl-2-methylpyridine and 96 g. of sulfur were heated at 160°–170° C. for 20 hours. The reaction mixture was dissolved in 2,000 ml. of chloroform and the solution was washed with water and 6 N hydrochloric acid successively. Chloroform was removed by evaporation in vacuo. The residue was subjected to silica gel column chromatography and recrystallized from ethyl acetate. The product showed no melting point depression upon mixing with the product of the preceding example. Yield, 137 g (61% of theory).

EXAMPLE 7

Preparation of 2-(6-ethylpyridin-2-yl)benzimidazole 2.2 g. of o-phenylenediamine, 3 g. of 6-ethylpicolinic acid and 15 g. of polyphosphoric acid were heated at 160°–180° C. under nitrogen gas current for 2 hours with stirring. The reaction mixture was diluted with 200 ml. of water and neutralized with sodium carbonate. The resulting precipitate was filtered off, dried, subjected to silica gel column chromatography (developed with 1:1 by volume mixture of benzene and ethyl acetate) and recrystallized from benzene. 3.3 g. of colorless needles of the product (74% of theory) was obtained. M.P. 161°–161.5° C.

Analysis, calculated for $C_{14}H_{13}N_3$: C, 75.31; H, 5.87; N, 18.82. Found: C, 75.52; H, 5.81; N, 18.72.

EXAMPLE 8

Preparation of 2-(5-butylpyridin-2-yl) benzimidazole 0.6 g. of o-phenylenediamine, 1 g. of fusaric acid and 10 g. of polyphosphoric acid were heated at 200°–250° C. under nitrogen gas current with stirring for 1.5 hours. The reaction mixture was diluted with 200 ml. of water and then neutralized with sodium carbonate. The resulting crystals were filtered off, dried and recrystallized from ethyl acetate. 1.2 g. of colorless needles of the product (86% of theory) was obtained. M.P. 138.0°–139.0° C.

EXAMPLE 9

Preparation of 2-(2-pyridyl)-5(6)-methylbenzimidazole 18.6 g. of toluylene-3,4-diamine, 18.8 g. of picolinic acid and 120 g. of polyphosphoric acid were heated at 160°–180° C. under nitrogen gas current with stirring for 2 hours. The reaction mixture was diluted with 1,000 ml. of water and then neutralized with sodium carbonate. The resulting crystals were filtered off, dried and recrystallized from benzene. 20 g. (62% of theory) of colorless needles of the product was obtained. M.P. 164.0°–165.0° C.

EXAMPLE 10

Preparation of 2-(5-methylpyridin-2-yl)-5(6)-methylbenzimidazole 2.1 g. of toluylene-3,4-diamine, 2.3 g. of 5-methylpicolinic acid and 15 g. of polyphosphoric acid were heated at 200° C. under nitrogen gas current with stirring for 2 hours. The reaction mixture was diluted with 200 ml. of water and then neutralized with sodium carbonate. The resulting precipitates were filtered off, dried, subjected to silica gel column chromatography (developed with benzene) and recrystallized from cyclohexane. 1.3 g. (58% of theory) of colorless needles of the product was obtained. M.P. 166.5°–167.0° C.

EXAMPLE 11

Preparation of 2-(6-methylpyridin-2-yl)-5(6)-methylbenzimidazole 7.0 g. of toluylene-3,4-diamine, 5.4 g. of 2,6-lutidine and 4.8 g. of sulfur were heated at 160°–170° C. for 5 hours. The reaction mixture was dissolved in 500 ml. of chloroform. The solution was washed with water, dried and evaporated in vacuo to remove the solvent. The residue was subjected to silica gel chromatography and recrystallized from 1:1 by volume mixture of benzene and n-hexane. 7.1 g. (68% of theory) of colorless needles of the product was obtined. M.P. 208.0°–209.5° C.

Analysis, calculated for $C_{14}H_{13}N_3$: C, 75.31; H, 5.87; N, 18.82. Found: C, 75.58; H, 5,85; N, 18.89

EXAMPLE 12

Preparation of 2-(5-ethylpyridin-2-yl)-5(6)-methylbenzimidazole 1.2 g. of toluylene-3,4-diamine, 1.5 g. of 5-ethylpicolinic acid and 10 g. of polyphosphoric acid were heated at 160°–180° C. under nitrogen gas current with stirring for 2 hours. The reaction mixture was diluted with 100 ml. of water and then neutralized with sodium carbonate. The resulting crystals were filtered off, dried, chromatographed through silica gel column and recrystallized from cyclohexane. 1.8 g. (77% of theory) of colorless needles of the product was obtained. M.P. 114.0°–115.0° C.

EXAMPLE 13

Preparation of 2-(2-pyridyl)-5(6)-methoxybenzimidazole 11.9 g. of 4-methoxy-o-phenylenediamine hydrochloride, 7 g. of picolinic acid and 40 g. of polyphosphoric acid were heated at 180°–190° C. under nitrogen gas current with stirring for 2 hours.

The reaction mixture was diluted with water and then neutralized with sodium carbonate. The resulting precipitates were filtered off, dried, chromatographed through silica gel column (developed with benzene) and recrystallized from 1:2 by volume mixture of ethyl acetate and n-hexane. 9.0 g. (71% of theory) of colorless needles of the product was obtained. M.P. 136.0°–137.5° C.

EXAMPLE 14

Preparation of 2-(5-ethylpyridin-2-yl)-5(6)-methoxybenzimidazole 10.6 g. of 4-methoxy-o-phenylenediamine hydrochloride, 7.6 g. of 5-ethylpicolinic acid and 40 g. of polyphosphoric acid were heated at 180°–190° C. under nitrogen gas current with stirring for 1 hour. The reaction mixture was diluted with 500 ml. of water and then neutralized with sodium carbonate. The precipitates were filtered off, dried, chromatographed through silica gel column (developed with benzene) and recrystallized from ligroin. 8.6 g. of colorless needles of the product (67% of theory) was obtained. M.P. 141.5°–142.0° C.

EXAMPLE 15

Preparation of 2-(6-methylpyridin-2-yl)-5(6)-methoxybenzimidazole 6.4 g. of 4-methoxy-o-phenylenediamine, 5 g. of 2,6-lutidine and 4.5 g. of sulfur were heated at 150°–160° C. for 1.5 hours.

To the reaction mixture was added 100 ml. of methanol. The precipitated sulfur was removed by filtering and the filtrate was evaporated in vacuo. The residue was chromatographed silica gel column and recrystallized from benzene. 9.2 g. of colorless needles of the product (82% of theory) was obtained. M.P. 189.0°–191.0° C.

EXAMPLE 16

Preparation of 2-(6-ethylpyridin-2-yl)-5(6)-methoxybenzimidazole 2.8 g. of 4-methoxy-o-phenylenediamine hydrochloride, 2.0 g. of 6-ethylpicolinic acid and 10 g. of polyphosphoric acid were heated at 160°–180° C. under nitrogen gas current with stirring for 2 hours. The reaction mixture was diluted with 100 ml. of water and then neutralized with sodium carbonate. The resulting precipiates were filtered off, chromatographed through silica gel column (developed with 8:2 mixture of benzene and ethyl acetate) and recrystallized from n-hexane. 2.4 g. (73% of theory) of colorless needles of the product was obtained. M.P. 147.5°–148.5° C.

EXAMPLE 17

Preparation of 2-(2-pyridyl)-5(6)-chlorobenzimidazole 2.5 g. of 4-chloro-o-phenylenediamine, 2.2 g of picolinic acid and 11 g. of polyphosphoric acid were heated at 170°–180° C. under nitrogen gas current with stirring for 2 hours. The reaction mixture was diluted with 100 ml. of water and then neutralized with sodium carbonate. The resulting precipitates were filtered off, dried, chromatographed through silica gel column (developed with 1:1 mixture of ethyl acetate and benzene) and recrystallized from cyclohexane. 2.6 g. (65% of theory) of colorless needles of the product was obtained. M.P. 141.5°–142.5° C.

EXAMPLE 18

Preparation of 2-(5-methylpyridin-2-yl)-5(6)-chlorobenzimidazole 7.8 g. of 4-chloro-o-phenylenediamine, 6.9 g. of 5-methylpicolinic acid and 40 g. of polyphosphoric acid were heated at 170°–180° C. under nitrogen gas current with stirring for 2 hours.

The reaction mixture was diluted with 500 ml. of water and then neutralized with sodium carbonate. The resulting crystals were filtered off, dried and recrystallized from benzene. 8.2 g (67% of theory) of colorless needles of the product was obtained. M.P. 171.0°–172.0° C.

EXAMPLE 19

Preparation of 2-(6-methylpyridin-2-yl)-5(6)-chlorobenzimidazole 7.2 g. of 4-chloro-o-phenylenediamine, 5.4 g. of 2,6-lutidine and 4.8 g. of sulfur were heated at 150°–160° C. with stirring for 6 hours. To the reaction mixture was added 100 ml. of methanol and the separated sulfur was removed by filtration. The filtrate was evaporated in vacuo. The residue was chromatographed through silica gel column and recrystallized from benzene. 8.9 g. (72% of theory) of colorless needles of the product was obtained. M.P. 173.5°–174.5° C.

Analysis, calculated for $C_{13}H_{10}N_3Cl$: C, 64.07; H, 4.14; N, 17.24; Cl, 14.55. Found: C, 64.28; H, 4.09; N, 17.30; Cl 14.36.

EXAMPLE 20

Preparation of 2-(5-ethylpyridin-2-yl)-5(6)-chlorobenzimidazole 7.2 g. of 4-chloro-o-phenylenediamine, 7.6 g. of 5-ethylpicolinic acid and 40 g. of polyphosphoric acid were heated at 170°–180° C. under nitrogen gas current with stirring for 2 hours.

The reaction mixture was diluted with 500 ml. of water and then neutralized with sodium carbonate. The resulting precipitates were filtered off, dried, chromatographed through silica gel column and recrystallized from cyclohexane. 8.9 g. (70% of theory) of colorless needles of the product was obtained. M.P. 169.5°–170.5° C.

EXAMPLE 21

Preparation of 2-(6-ethylpyridin-2-yl)-benzimidazole 1.1 g. of o-phenylenediamine and 1.3 g. of freshly distilled 6-cyano-2-ethylpyridine were dissolved in 5 ml. of DMF. To the solution was added 0.05 g. of sodium in 1 ml. of methanol. The mixture was stirred at 60° C. for 30 minutes, then acidified with acetic acid and stirred again at 100° C. for an additional 1 hour. The reaction mixture was poured in 100 ml. of water. The resulting crystals were filtered off dried and recrystallized from benzene. 1.7 g. (78% of theory) of the product was obtained.

This product was identical to the product of Example 7.

EXAMPLE 22

Preparation of 2-(5-ethylpyridin-2-yl)-benzimidazole 1.1 g. of o-phenylenediamine and 1.3 g. of 2-cyano-5-ethylpyridine were dissolved in 5 ml. of methanol. To the solution was added 0.05 g. of sodium in 1 ml. of methanol. The mixture was refluxed for 2 hours, then acidified with acetic acid and refluxed again for additional 4 hours. The reaction mixture was evaporated.

The residue was washed with water, dried and recrystallized from ethyl acetate. 1.5 g. (72% of theory) of the product which was identical to the product of Example 5 was obtained.

EXAMPLE 23

Preparation of 2-(p-ethylphenyl) benzimidazole 5.5 g. of o-phenylenediamine, 7.6 g. of p-ethylbenzoic acid and 40 g. of polyphosphoric acid were heated at 160°–180° C. under nitrogen gas current with stirring for 4 hours. The reaction mixture was diluted with 400 ml. of water and then neutralized with sodium carbonate. The resulting crystals were filtered off, dried and recrystallized from ethyl acetate. 8.2 g. (73% of theory) of the product was obtained. M.P. 258°–258.4° C.

In the same way as described, the following compounds were prepared from a corresponding o-phenylenediamine and an appropriately substituted benzoic acid:

2-(p-isopropylphenyl) benzimidazole, M.P. 250°–252.5° C.;

2-(p-t-butylphenyl) benzimidazole, M.P. 252.5°–253.5° C.;

2-(o-ethylphenyl)benzimidazole, M.P. 207°–208° C.;

2-(p-ethylphenyl)-5(6)-chlorobenzinidazole, M.P. 199.5°–200.5° C.;

2-(p-ethylphenyl)-5(6)-methylbenzimidazole, M.P. 191.5°–192.5° C.;

2-(m-ethylphenyl)benzimidazole, M.P. 202°–203° C.;

2-(o-ethylphenyl)-5(6)-chlorobenzimidazole, M.P. 183°–184° C.

EXAMPLE 24

Preparation of 2-(p-ethylphenyl)-5(6)-methoxybenzimidazole 8.0 g. of 4-methoxy-o-phenylenediamine hydrochloride, 6.0 g. of p-ethylbenzoic acid and 40 g. of polyphosphoric ester were heated at 120° C. with stirring for 1 hour. The reaction mixture was diluted with water and then neutralized with sodium carbonate.

The mixture was extracted with ethyl acetate and the extract was evaporated in vacuo. The resulting crystals were recrystallized from acetonitrile. 3.4 g. (68% of theory) of the product was obtained. M.P. 160°–161° C.

In the same was as described, the following compounds were prepared from a corresponding o-phenylenediamine and an appropriately substituted benzoic acid:

2-(o-ethylphenyl)-5(6)-methoxybenzimidazole, M.P. 121°–122° C.;
2-(o-ethylphenyl)-5(6)-methylbenzimidazole, M.P. 166°–166.7° C.

EXAMPLE 25

Preparation of 2-(m-ethylphenyl)benzimidazole 2.2 g. of o-phenylenediamine and 3.1 g. of m-ethylenbenzonitrile were dissolved in 30 ml. of methanol. To the solution was added 1.1 g. of sodium methoxide in methanol. The mixture was stirred at 60° C. for 2 hours, acidified with acetic acid, stirred again at 100° C. for additional 3 hours and poured in 100 ml. of water. The resulting crystals were filtered off, dried and recrystallized from ethyl acetate. 2.7 g. of the product (60% of theory) was obtained. The product was identical to that obtained in Example 23.

EXAMPLE 26

Preparation of 2-(o-ethylphenyl)-5(6)-methylbenzimidazole 5.0 g. of p-toluidine, 6.2 g. of o-ethylbenzonitrile and 6.3 g. of anhydrous aluminum chloride were heated at 120° C. with stirring for 1 hour. To the reaction mixture was added water and sodium hydroxide to make the mixture alkaline. The mixture was extracted with benzene and the extract was washed with water, dried and evaporated in vacuo to remove benzene. 10.2 g. (92% of theory) of N-(p-methylphenyl)-2-ethylbenzamidine was obtained.

5.0 g. of this product was added aqueous methanol and the mixture was acidified with hydrochloric acid. To the mixture were added an aqueous solution of sodium hypochlorite until potassium iodide - starch paper turns blue.

The mixture was then made alkaline with sodium carbonate, refluxed for 2.5 hours and cooled to room temperature. The resulting crystals were filtered off, dried and recrystallized from benzene, whereby 3.9 g. (80% of theory) of the product was obtained.

The product was identical to that obtained in Example 24.

EXAMPLE 27

Preparation of 2-(p-ethylphenyl)-5(6)-methoxybenzimidazole 5.0 g. of p-ethylbenzonitrile in 40 ml. of methanolic hydrochloric acid was stirred at room temperature over night.

The reaction mixture was diluted with water, neutralized with sodium carbonate and extracted with n-hexane. The extract was evaporated in vacuo to remove n-hexane. The remaining alkoxyimine compound was taken in methanol and 4.7 g. of p-anisidine was added thereto. The mixture was warmed for 30 minutes and evaporated in vacuo to remove methanol, whereby N-(p-methoxyphenyl)-4-ethylbenzamidine was produced. This product was dissolved in water and then acidified with hydrochloric acid. To this solution was added an aqueous solution of sodium hypochlorite until potassium iodide-starch paper turns blue.

The mixture was extracted with methylenechloride. The extract was washed with water, dried and evaporated at a lower temperature.

The residue was dissolved in 100 ml. of 50% aqueous methanol and 6.0 g. of sodium carbonate in small amount of water was added thereto. The solution was refluxed for 1 hour and evaporated in vacuo to remove methanol. The resulting crystals were filtered off, dried and recrystallized from acetonitrile, whereby 7.0 g. (73% of theory) of the product was obtained.

The product was identical to that obtained in Example 24. It is to be understood that the foregoing detailed description is given merely by way of illustration and that many variations may be made therein without departing from the spirit of the present invention.

We claim:

1. A compound of the formula:

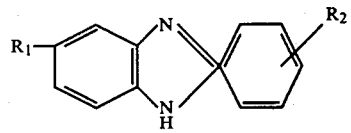

wherein $R_1$ is hydrogen, halogen, $C_1$–$C_4$ alkyl or $C_1$–$C_4$ alkoxy and $R_2$ is ethyl or tert-butyl.

2. A compound according to claim 1, 2-(p-tert-butylphenyl)benzimidazole.

3. A compound according to claim 1, 2-(p-ethylphenyl)benzimidazole.

4. A compound according to claim 1, 2-(m-ethylphenyl)-5(6)-methoxy-benzimidazole.

5. A compound according to claim 1, 2-(o-ethylphenyl)-5(6)-methoxy-benzimidazole.

6. A compound according to claim 1, 2-(m-ethylphenyl)benzimidazole.

7. A pharmaceutical composition for use in treating inflammation comprising an anti-inflammatory effective amount of a compound according to claim 1 in admixture with a pharmaceutically acceptable carrier.

8. A pharmaceutical composition according to claim 7, wherein said compound is 2-(p-tert-butylphenyl) benzimidazole.

9. A pharmaceutical composition according to claim 7, wherein said compound is 2-(p-ethylphenyl) benzimidazole.

10. A pharmaceutical composition according to claim 7, wherein said compound is 2-(m-ethylphenyl) benzimidazole.

11. A pharmaceutical composition according to claim 7, wherein said compound is 2-(o-ethylphenyl)-5 (6)-benzimidazole.

12. A pharmaceutical composition according to claim 7, wherein said compound is 2-(m-ethylphenyl)-5 (6)-benzimidazole.

* * * * *